United States Patent
Zhang et al.

(10) Patent No.: US 9,014,341 B2
(45) Date of Patent: Apr. 21, 2015

(54) CT COLLIMATOR AND CT SYSTEM INCLUDING THE CT COLLIMATOR

(71) Applicant: GE Medical Systems Global Technology Company, LLC, Waukesha, WI (US)

(72) Inventors: Xiaoyan Zhang, Beijing (CN); Jun Guo, Beijing (CN); Xuyong Yang, Beijing (CN)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 45 days.

(21) Appl. No.: 14/071,178

(22) Filed: Nov. 4, 2013

(65) Prior Publication Data
US 2014/0146948 A1    May 29, 2014

(30) Foreign Application Priority Data
Nov. 27, 2012    (CN) .......................... 2012 1 0489931

(51) Int. Cl.
*G21K 1/02*    (2006.01)
*A61B 6/03*    (2006.01)
*A61B 6/06*    (2006.01)
*A61B 6/00*    (2006.01)

(52) U.S. Cl.
CPC ..... *G21K 1/02* (2013.01); *A61B 6/03* (2013.01); *A61B 6/06* (2013.01); *A61B 6/4021* (2013.01); *A61B 6/467* (2013.01); *A61B 6/547* (2013.01)

(58) Field of Classification Search
CPC .................................. A61B 6/035; A61B 6/06
USPC ...................................... 378/4, 147; 250/394
See application file for complete search history.

(56) References Cited

U.S. PATENT DOCUMENTS

2014/0140471 A1 *    5/2014    Tybinkowski et al. .......... 378/19

* cited by examiner

*Primary Examiner* — Michael Maskell
(74) *Attorney, Agent, or Firm* — Mark A. Conklin; GE Global Patent Operation (57) ABSTRACT

A CT collimator comprising a rotating slot part on a rotation shaft and having a plurality of blades, each blade has a slot of a different width and a radiation beam entering the collimator can only pass via a slot in one of the blades, each edge of each blade slot along a longitudinal direction has a convex curved surface structure, and in a vertical plane along a longitudinal direction, two side edges of the slot are curved, and each blade is arranged to be eccentric to the center of the rotation shaft. A CT system using the CT collimator, the detection area of the radiation rays projected to the radiation detector via the CT collimator can be maintained unchanged by adjusting the rotation angle of the blade, under the circumstance where the focus of the radiation source shifts during a CT scan.

19 Claims, 8 Drawing Sheets

CT COLLIMATOR AND CT SYSTEM INCLUDING THE CT COLLIMATOR

BACKGROUND TO THE INVENTION

The present application relates to the field of radiograph CT, and more particularly, to a CT collimator having a single motor drive system and a radiograph CT system having the CT collimator.

At present, radiograph CT systems such as X-ray CT system are widely used in various medical institutions for three-dimensional imaging of the regions of interest of the subjects to assist the clinicians to achieve an accurate medical diagnosis of the subjects.

In a radiograph CT system, a radiation tube generating cone-shaped radiation beams and a detector detecting the radiation beams rotate around a rotation center, wherein the detector is disposed opposite to the radiation tube and consists of detector elements arranged in a matrix form. Projection data generated by the radiation beams transmitting through the subject are collected; based on the collected projection data, an image of the region of interest of the subject is reconstructed; and then the reconstructed CT image is displayed on an image display device.

In a radiograph CT system, a collimator is generally provided between the radiation tube and the subject to be detected. By adjusting a width of the aperture of the collimator, the width of the radiation beams in a direction parallel to the subject is controlled so as to control a thickness of the scan.

A conventional collimator generally has at least two different motor drive systems to meet the requirements of multi-slot opening and Z-beam tracking. Such a collimator comprises at least two gates or cams, which are driven by at least two different motor drive systems, and hence have higher cost.

Some newly developed collimators use a single motor drive system to meet the requirements of slot opening and Z-beam tracking. For example, a recently developed collimator comprises a plate having a plurality of slots driven by a single motor drive system. Each slot corresponds to a collimator aperture of a different width. Though using a single motor drive system in place of the conventional two drive systems to reduce the cost of the drive system, such a collimator requires converting the rotational motion of the motor into a linear motion and hence the need of such components as lead screw and rails. Therefore, there is a need for a CT collimator and a CT system that, in case of a focus shift of the radiation source due to temperature changes during a CT scan, can automatically correct the position of the collimator aperture and enable the radiation beams to be irradiated to the subject via the collimator directly in a rotational movement manner without departing from the predetermined region of interest so that the detection area of the radiation beams projected to the detector after passing through the subject remains unchanged.

SUMMARY OF THE INVENTION

Embodiments of the present invention provide a CT collimator and a CT system comprising the CT collimator capable of solving the above problems.

According to a first aspect of the present invention, there is provided a CT collimator. The CT collimator comprises a rotating slot part disposed on a rotation shaft and having a plurality of blades, wherein each blade has a slot of a different width and a radiation beam entering the collimator can only pass via a slot in one of the plurality of blades, wherein an edge of each blade slot along a longitudinal direction of this blade has a convex curved surface structure, and in a vertical plane along a longitudinal direction of each blade slot, the two side edges of the slot are curved, and wherein each blade is arranged to be eccentric to the center of the rotation shaft.

The CT collimator according to an embodiment of the present invention further comprises a single motor configured to drive the rotating slot part to rotate around the rotation shaft; and an encoder for monitoring an angle of rotation of the rotating slot part around the center of the rotation shaft.

The CT collimator according to an embodiment of the present invention further comprises a single motor configured to drive the rotating slot part to rotate around the rotation shaft, wherein the single motor is provided with an encoder for monitoring an angle of rotation of the rotating slot part around the center of the rotation shaft.

In the CT collimator according to an embodiment of the present invention, the curved surface structure of each blade edge comprises two curved lines in a vertical plane along the longitudinal direction of this blade, and a blade slot of this blade allows radiation beams between radiation lines tangent to the two curved lines to pass through.

In the CT collimator according to the an embodiment of the present invention, the curved surface structure of each blade edge comprises two circular arcs in a vertical plane along the longitudinal direction of this blade, and a blade slot of this blade allows radiation beams between radiation lines tangent to the two circular arcs to pass through.

In the CT collimator according to an embodiment of the present invention, two circles for the two circular arcs are respectively: when, in the vertical plane, the rotation of a first connecting line and a second connecting line between a maximum shift position to the left of a radiation source and left and right edge points of a radiation detection area of a radiation detector around the center of the rotation shaft relative to a third connecting line and a fourth connecting line between a maximum shift position to the right of the radiation source and the left and right edge points of the radiation detection area reaches a position where there are respective intersections in a blade thickness region between the first connecting line and the third connecting line and between the second connecting line and the fourth connecting line, a first circle that is tangent to the first connecting line and the third connecting line at said position, and a second circle that is tangent to the second connecting line and the fourth connecting line at said position.

In the CT collimator according to an embodiment of the present invention, each blade has a planar structure, and a width of a slot of each blade gradually increases from the center of the slot to the two ends along the longitudinal direction of the blade.

In the CT collimator according to an embodiment of the present invention, when each blade has an arc structure whose center of circle is on a focal point of a radiation source outside the collimator when this blade is located in the horizontal position.

In the CT collimator according to an embodiment of the present invention, when the center of the rotation shaft is not located in an extended region of each blade slot along the thickness direction of the blade, said blade is eccentric to the center of the rotation shaft.

According to an embodiment of the present invention, there is provided a CT system. The CT system comprises a CT collimator according to the first aspect of the present invention, a radiation detection area monitoring unit disposed on a radiation detector, and a collimator controller that selects one of a plurality of blades of the rotating slot part according to a region of interest of a subject to allow a desired radiation beam to be projected to the region of interest of the subject, wherein the radiation detection area monitoring unit monitors, during a CT scan, an offset of the radiation detection area on the radiation detector caused by focus shift of the radiation source as radiation beam is projected to the radiation detector via the selected blade of the CT collimator, and wherein the collimator controller is configured to correct an angle of rotation of the rotating slot part of the CT collimator according to the monitored offset received from the radiation detection area monitoring unit to eliminate the offset of the radiation detection area caused by the focus shift of the radiation source for performing Z-beam tracking.

The CT system according to an embodiment of the present invention is an X-ray CT system.

In the CT system according to an embodiment of the present invention, the collimator controller comprises a memory or is coupled to a memory.

In the CT system according to an embodiment of the present invention, a plurality of offsets of the radiation detection area predetermined for each blade in the rotating slot part and a plurality of corresponding correction angles that the rotating slot part is required to rotate for performing Z-beam tracking are stored in the form of a table in the memory.

In the CT system according to an embodiment of the present invention, the collimator controller is configured to: determine a rotation correction angle of the rotating slot part for the selected blade through a search in said table in said memory according to the monitored offset of the radiation detection area, and perform Z-beam tracking according to the determined rotation correction angle of the rotating slot part and the current angle of the selected blade.

In the CT system according to an embodiment of the present invention, the collimator controller is configured to: in case of failure to find a corresponding rotation correction angle of the rotating slot part in said table according to the monitored offset of the radiation detection area, search for two rotation correction angles corresponding to two offsets close to the monitored offset of the radiation detection area, and use an average of the two rotation correction angles or an interpolation therebetween as the determined rotation correction angle of the rotating slot part; or in case of failure to find a corresponding rotation correction angle of the rotating slot part in said table according to the monitored offset of the radiation detection area, search for a rotation correction angle corresponding to the shift closest to the monitored offset of the radiation detection area and use it as the determined rotation correction angle of the rotating slot part.

In the CT system according to an embodiment of the present invention, a plurality of focus shifts of the radiation source predetermined for each blade in the rotating slot part and a plurality of rotation correction angles of the rotating slot part required for Z-beam tracking are stored in the form of a table in the memory.

In the CT system according to an embodiment of the present invention, the collimator controller is configured to: determine a focus shift of the radiation source according to the monitored offset of the radiation detection area, determine a rotation correction angle of the rotating slot part for the selected blade through a search in said table in said memory according to the determined focus shift, and perform Z-beam tracking according to the determined rotation correction angle of the rotating slot part and the current angle of the selected blade.

In the CT system according to an embodiment of the present invention, the collimator controller is configured to: in case of failure to find a corresponding rotation correction angle of the rotating slot part in said table according to the determined focus shift, search for two rotation correction angles corresponding to two focus shifts close to the determined focus shift, and use an average of the two rotation correction angles or an interpolation therebetween as the determined rotation correction angle of the rotating slot part; or in case of failure to find a corresponding rotation correction angle of the rotating slot part in said table according to the determined focus shift, search for a rotation correction angle corresponding to the focus shift closest to the determined focus shift and use it as the determined rotation correction angle of the rotating slot part.

In the CT system according to an embodiment of the present invention, the collimator controller is further configured to, after correction of a rotation angle of the rotating slot part of the CT collimator, compare a latest monitored offset of the radiation detection area received from the radiation detection area monitoring unit with a predetermined threshold, and if the latest monitored offset of the radiation detection area does not exceed the predetermined threshold, then stop the Z-beam tracking; or if the latest monitored offset of the radiation detection area exceeds the predetermined threshold, then perform a new Z-beam tracking until the latest monitored offset of the radiation detection area does not exceed the predetermined threshold.

In the CT collimator and CT system comprising said CT collimator according to embodiments of the present invention, a plurality of blades having variable slot widths can be provided in the CT collimator according to the needs of a CT scan. An edge of each blade slot along a longitudinal direction of the blade has a convex curved surface structure (namely, in a vertical plane along a longitudinal direction of the blade slot, the two side edges of the slot are curved) so that when a focus shift of the radiation source along a focus shift path occurs as a result of temperature change, by rotating the selected blade about the rotation center eccentric to the blade a correction angle corresponding to the focus shift, the radiation beams reaching the radiation detector via the blade slot are maintained at the same region as the circumstance where focus shift does not occur. Therefore, the CT collimator and CT system according to an embodiment of the present invention eliminate the need to relocate other components such as the radiation detector or the subject when a focus shift of the radiation source occurs.

BRIEF DESCRIPTION OF THE DRAWINGS

In the following some exemplary embodiments of the present invention will be described in detail with reference to the accompanying drawings, in which like or similar elements are denoted by the same reference numerals, wherein.

DETAILED DESCRIPTION OF THE INVENTION

In the following detailed description, exemplary embodiments of the present invention are described with reference to the accompanying drawings. However, it will be appreciated by persons skilled in the art that the present invention is not limited to these exemplary embodiments.

Figure 1A:
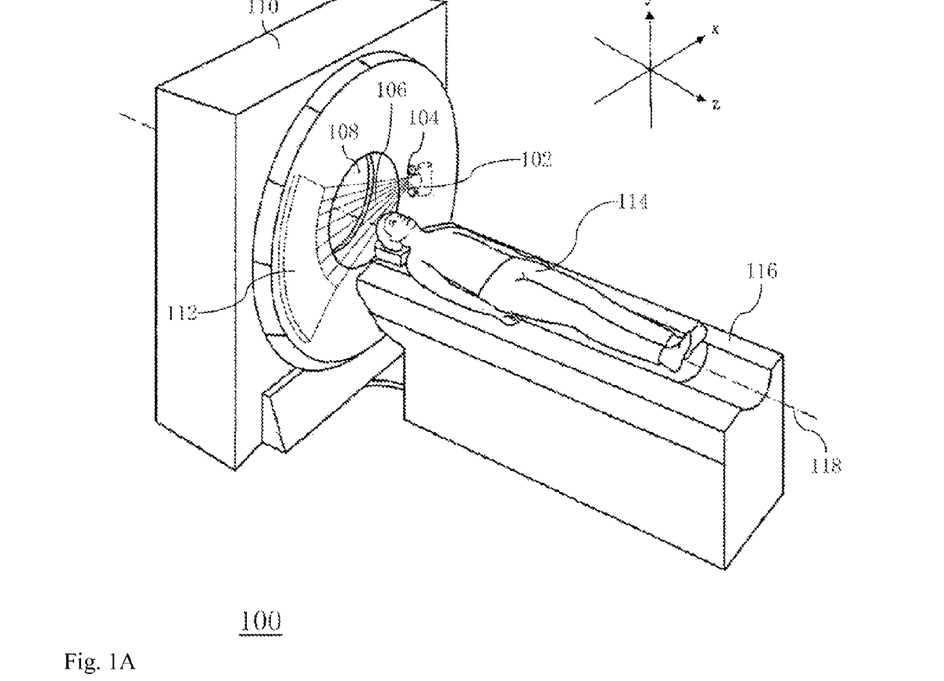
FIGS. 1A and 1B show a radiograph CT system according to an exemplary embodiment of the present invention.
Figure 1B:
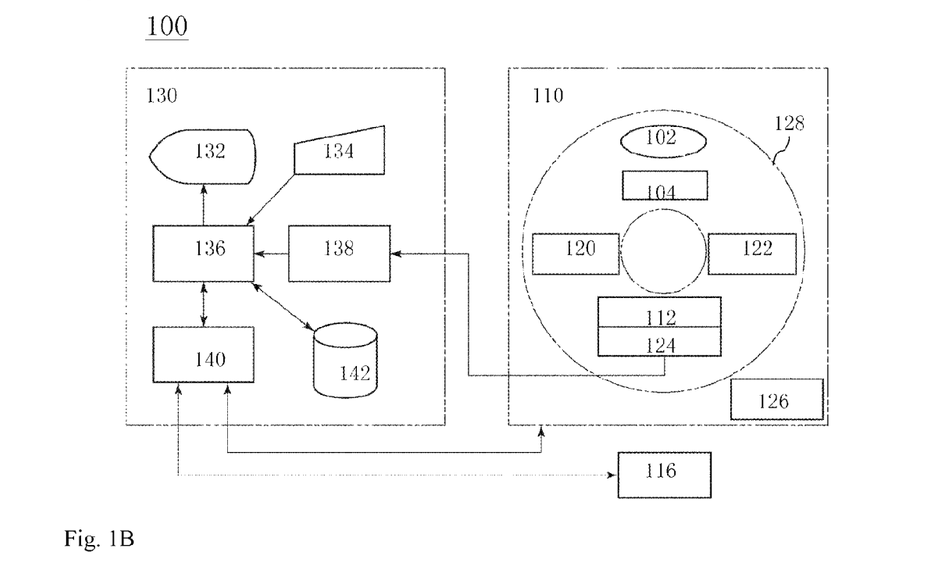

FIGS. 1A and 1B show a radiograph CT system 100 according to an exemplary embodiment of the present invention. In an embodiment, the radiograph CT system 100 is an X-ray CT system.

As shown in FIGS. 1A and 1B, the X-ray CT system 100 mainly includes three parts: a scan gantry 110, a support table 116 for positioning a subject 114 to be detected, and an operation console 130. The scan gantry 110 includes an X-ray tube 102. X-rays 106 emitted from the X-ray tube 102 pass through a collimator 104 to form an X-ray beam of such shapes as fan shaped beam and cone shaped beam, to be irradiated to a region of interest of the subject 114. The X-ray beam that passes through the subject 114 is applied to an X-ray detector 112 disposed on the other side of the subject 114. The X-ray detector 112 has a plurality of two-dimensional X-ray detecting elements in the propagation direction (the signal channel direction) and the thickness Z direction (column direction) of the fan-shaped X-ray beam.

A data acquisition system (DAS) 124 is coupled to the X-ray detector 112. The data acquisition system 124 collects the data detected by each of the X-ray detecting elements of the X-ray detector 124 for using as the projection data. The X-ray radiation from the X-ray tube 102 is controlled by an X-ray controller 122. In FIG. 1B, the connections between the X-ray tube 102 and the X-ray controller 122 are not shown.

The data acquisition system 124 collects data related to the tube voltage and tube current applied to the X-ray tube 102 by the X-ray controller 122. In FIG. 1B, the connections between the X-ray controller 122 and the data acquisition system 124 are omitted.

The collimator 104 is controlled by a collimator controller 120. In an embodiment, the collimator 104 and the collimator controller 120 are two separate components. In an embodiment, the collimator controller 120 may be disposed within the collimator 104. In FIG. 1B, the connections between the collimator 104 and the collimator controller 120 are omitted.

Components like the X-ray tube 102, the collimator 104, the X-ray detector 112, the data acquisition system 124, the X-ray controller 122 and the collimator controller 120 are mounted in a rotating portion 128 of the scan gantry 110. The rotating portion 128 rotates under the control of a rotation controller 126. In FIG. 1B, the connections between the rotating portion 128 and the rotation controller 126 are not shown.

Under the action of a drive system such as a motor, the support table 116 can be moved together with the subject 114 carried thereon along a longitudinal axis 118 of the subject into an opening 108 of the scan gantry 110, so that the region of interest of the subject 114 is substantially perpendicular to the X-ray beam irradiated thereon through the collimator 104.

The operation console 130 has a central processor 136 such as a computer. A control interface 140 is connected to the central processor 136. The scan gantry 110 and the support table 116 are connected to the control interface 140. The central processor 136 controls the scan gantry 110 and the support table 116 via the control interface 140.

The data acquisition system 124, the X-ray controller 122, the collimator controller 120 and the rotation controller 126 in the scan gantry 110 are controlled via the control interface 140. In FIG. 1B the separate connections between the relevant parts and the control interface 140 are not shown.

A data acquisition buffer 138 is connected to the central processor 136. The data acquisition system 124 of the scan gantry 110 is connected to the data acquisition buffer 138. Projection data collected by the data acquisition system 124 are inputted to the central processor 136 via the data acquisition buffer 138.

The central processor 136 uses the projection data inputted from the data acquisition buffer 138 to perform an image reconstruction. In performing image reconstruction, such methods as the filtered back projection method, and three-dimensional image reconstruction method can be used. A storage device 142 is connected to the central processor 136. The storage device 142 may be used to store data, reconstructed images and procedures for implementing the various functions of the X-ray CT system 100.

A display device 132 and an input device 134 are connected to the central processor 136, respectively. The display device 132 displays the reconstructed images and other information output from the central processor 136. An operator can input various instructions and parameters to the central processor 136 via the input device 134. Through the display device 132 and the input device 134, the operator can achieve an interactive operation of the X-ray CT system 100.

Figure 2:
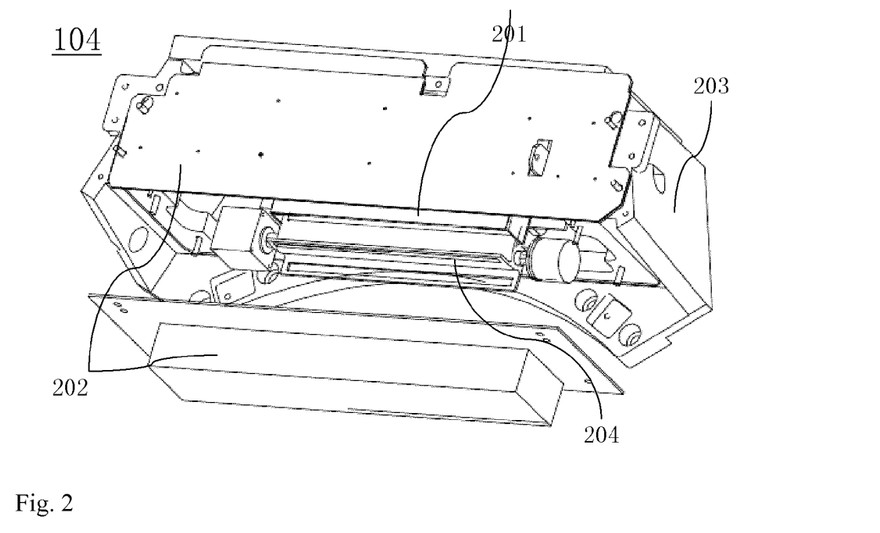
FIG. 2 shows a CT collimator according to an exemplary embodiment of the present invention.

FIG. 2 shows a schematic structural diagram of a radiograph CT collimator 104 according to an exemplary embodiment of the present invention. As shown in FIG. 2, the collimator 104 includes four main parts: a collimator case 203, a collimator cover 202, a filter assembly 201 and an aperture assembly 204. The aperture assembly 204 selects blades of different slot widths to allow the desired X-ray beam to reach the X-ray detector 112. The filter assembly 201 filters the X-ray beams from the X-ray tube 104 to eliminate the scattered X-ray beams. The collimator case 203 is used for supporting, fixing and housing various components of the collimator 104. The collimator cover 202 provides shielding for the collimator 104.

Figure 3A:
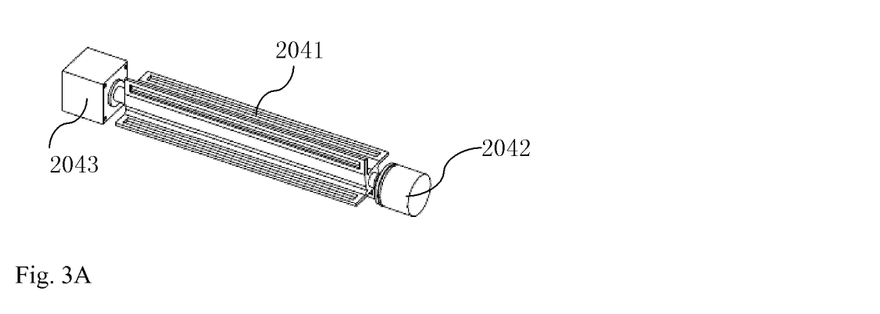
FIGS. 3A, 3B, 3C, and 3D show an aperture assembly in a CT collimator according to an exemplary embodiment of the present invention.

FIGS. 3A, 3B, 3C, and 3D show an exemplary structure of the aperture assembly 204 shown in FIG. 2. As shown in FIG. 3A, the aperture assembly 204 mainly includes three parts: a rotating slot part 2041, a single motor drive system 2043 driving the rotation of the rotating slot part 2041, and an encoder 2042 detecting the rotation angle of the rotating slot part 2041. In an embodiment, the motor drive system 2043 and the encoder 2042 are two separate parts. In an embodiment, the encoder 2042 may be disposed within the motor drive system 2043. The rotating slot part 2041 and the encoder 2042 can rotate together when driven by the motor drive system 2043.

Since the rotating slot part 2041 is directly driven by the motor drive system 2043, no rails, ball screw or lead screw are needed to convert the rotational motion into a linear motion, thereby simplifying the mechanical structure of the drive system of the collimator 104.

Figure 3B:
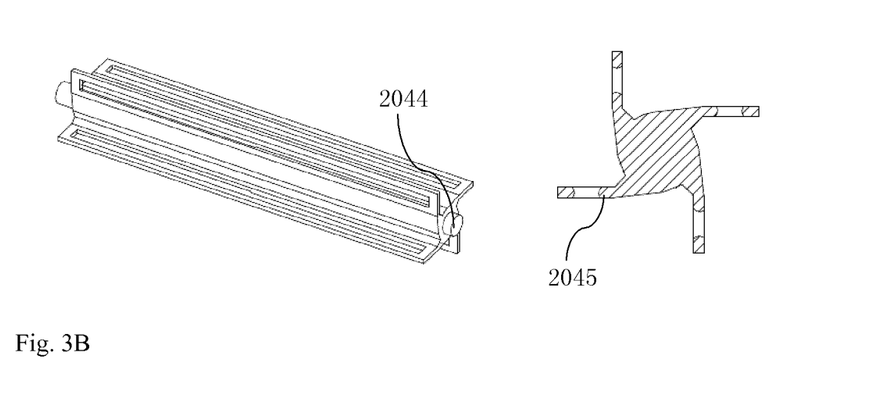

FIG. 3B shows an exemplary structure of the rotating slot part 2041 shown in FIG. 3A, and provides a cross-sectional view of the rotating slot part 2041 in a direction perpendicular to a longitudinal direction of the rotating slot part. As shown in FIG. 3B, the rotating slot part 2041 includes a rotation shaft 2044 and a plurality of blades 2045 fixed to the rotation shaft 2044 and rotating together with the rotation shaft 2044. Each blade has a slot of a different width and is provided with a shielding material to block the undesired X-ray beam entering the collimator 104, so that the X-ray beam can only pass via the slot in the blade for being irradiated to the region of interest of the subject 114.

The rotating slot part 2041 as shown in FIG. 3B has four blades and therefore four different slot widths. The four blades may be disposed around the rotation shaft 2044 in an evenly spaced or unevenly spaced manner. The number of blades on the rotating slot part 2041 can be determined according to actual needs, and can be set to, for example, 2, 3, 4, 5, etc.

Figure 3C:
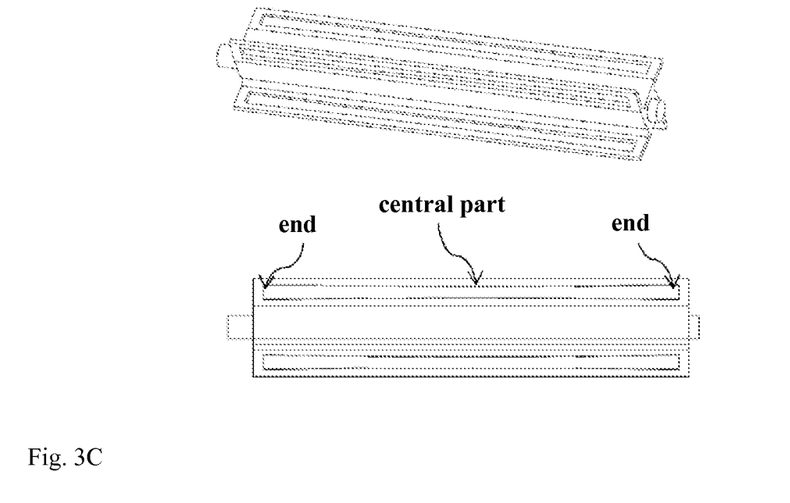

In an embodiment, each blade has a planar structure, and as shown in FIG. 3C, the width of the slot of each blade gradually increases from the center of the slot to the two ends along the longitudinal direction of the blade. In an embodiment, each blade and the blade slot have an arc structure whose center of circle, like the arc structure of the X-ray detector 112 disposed on the other side of the subject 114, is on the focal point of the X-ray tube 102.

Figure 3D:
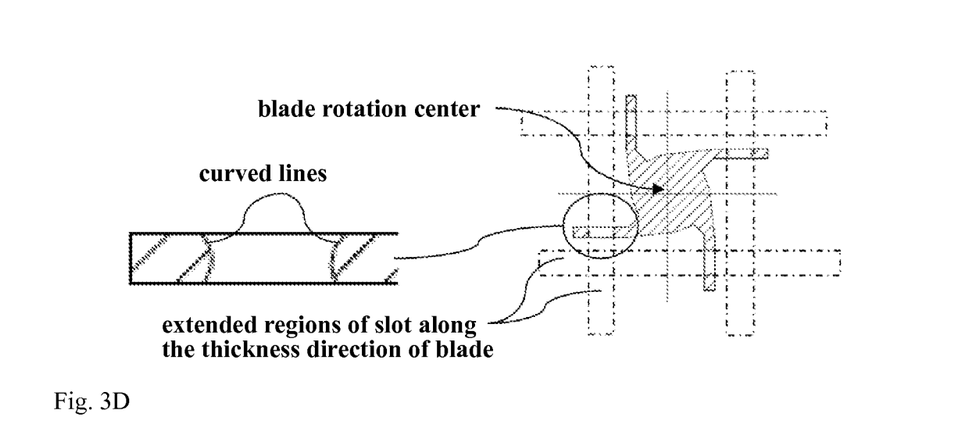

The two edges of each blade slot has a convex curved surface structure along the longitudinal direction of the blade. As shown in FIG. 3D, the edges of the slot of each blade 2045 has a curved shape in the cross sectional view along a thickness direction perpendicular to the longitudinal direction of the blade. Each blade is disposed to be eccentric to the rotation center of the rotating slot part 2041, so that the blade rotation center is not in an extended region of the slot along the thickness direction of the blade. As described below, by configuring the edges of each blade blot as having a convex curved surface structure, and allowing each blade to be eccentric to the rotation center of the rotating slot part 2041, it is possible to maintain the X-ray detection area on the X-ray detector 112 unchanged through adjustment of the rotating angle of the blade when the focus of the X-ray tube 102 shifts.

When carrying on a CT examination on the subject 114, the operator selects a slot width of the aperture assembly 204 of the collimator 104 via the input device 134. A control command is sent from the central processor 136 to the collimator controller 120. Under the action of the collimator controller 120, the motor drive system 2043 causes the blade of the rotating slot part 2041 having the desired slot width to rotate to a substantially horizontal position so that said blade is substantially perpendicular to the central X-ray beam emitted from the X-ray tube. Thus, X-ray beams entering the collimator 104 can only be irradiated to the region of interest of the subject 114 through the slot of said blade and pass through the subject 114 for being projected to the X-ray detector 112, thereby forming an X-ray detection area.

During operation, the focus of the X-ray tube 102 will shift as the tube temperature changes. Where the position of the selected blade of the collimator 104 remains unchanged, as compared with the circumstance where no focus shift takes places, a corresponding shift will occur to the X-ray beam irradiated to the subject 114 via the blade slot, which eventually results in a relatively large offset of the X-ray detection area on the X-ray detector 112.

Figure 5:
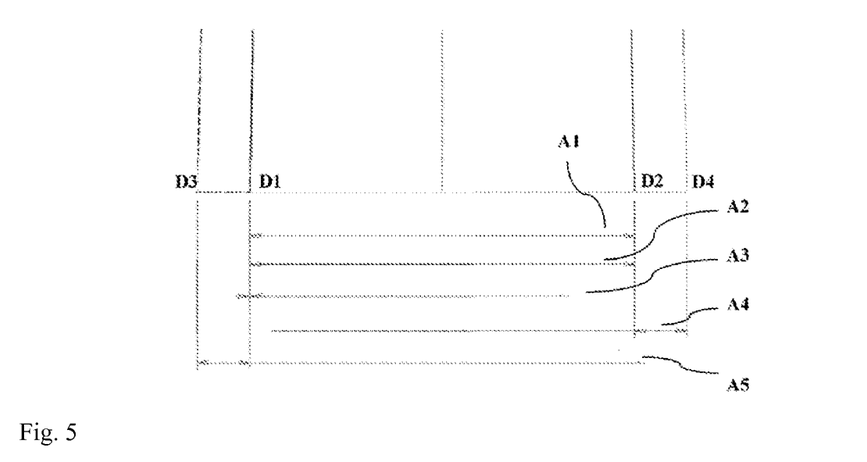
FIG. 5 shows an offset of the X-ray detection area on the X-ray detector when focus shift of the X-ray tube occurs and no Z-beam tracking is employed in the collimator.

As shown in FIG. 5, in case of no focus shift of the X-ray tube 102 during a CT scan, the X-ray detection area between the left edge D1 and the right edge D2 of the X-ray beam projected to the X-ray detector 112 via the slot of the selected blade of the collimator 104 is represented by A1. When the focus of the X-ray tube shifts due to temperature change during a CT scan along a focus shift path to the left edge of the focus shift path, the change of the X-ray detection area for the X-ray beam projected to the X-ray detector 112 via the slot of the selected blade is represented by A4. As shown, the right edge of the X-ray detection area of the X-ray detector 112 offsets from point D2 to point D4. Similarly, when due to temperature change the focus of the X-ray tube 102 shifts along a focus shift path to the right edge of the focus shift path, the change of the X-ray detection area for the X-ray beam projected to the X-ray detector via the blade slot is represented by A5. As shown, the left edge of the X-ray detection area of the X-ray detector 112 offsets from point D1 to point D3. Therefore, when focus shift occurs to the X-ray tube 102, if the position of the selected blade of the collimator 104 is not corrected, namely, not to perform Z-beam tracking, then the detection area for the X-ray beam projected to the X-ray detector 112 via the selected blade of the collimator 104 will deviate from the X-ray detection area A1 when focus shift does not occur to the X-ray tube 102.

In an embodiment, the curved lines of the curved surface structure of each blade slot edge in the cross-sectional view along a thickness direction perpendicular to the longitudinal direction of the blade as shown in FIG. 3D are circular arcs, wherein the circular arc close to the rotation center of the blade is referred to as an inner circular arc, and the circular arc away from the rotation center of the blade is referred to as an outer circular arc.

In the following, embodiments of the present invention will be further explained by taking the example where the curved lines of the curved surface structure of each blade slot edge in a vertical plane along the longitudinal direction of the blade slot are circular arcs. The skilled person will appreciate that the curved lines of the curved surface structure of each blade slot edge in a vertical plane along the longitudinal direction of the blade slot may be elliptical arcs or any other curved lines.

In an embodiment, an unequal angle tracking method as described below with reference to FIGS. 4A, 4B, 4C, and 4D can be used to determine the inner and outer circular arcs of the blade slot. For convenience of explanation, a cross-sectional view of the blade slot center along a thickness direction perpendicular to the longitudinal direction of the blade is used as an example for illustration.

Figure 4A:
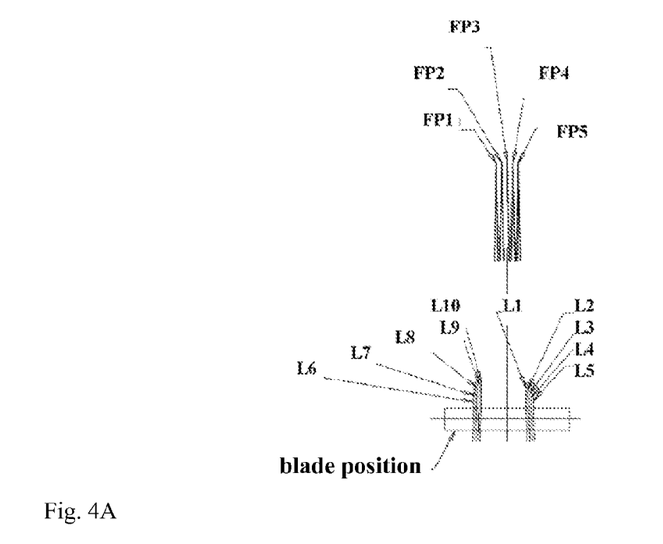
FIGS. 4A, 4B, 4C, and 4D illustrate a method for determining an inner circular arc and an outer circular arc of a blade slot in an aperture assembly in a CT collimator according to an exemplary embodiment of the present invention.

FIG. 4A shows exemplary focus positions FP1-FP5 of the X-ray tube 102 and edge lines L1-L10 of the X-ray beam when the X-ray beam emitted from the X-ray tube 102 at these focus positions is projected to the X-ray detector 112 via the blade slot, wherein focus positions FP1 and PF5 represent the largest shifts of the focus of the X-ray tube 102 along the focus shift path. The focus shift path and range of the X-ray tube are determined by its structure and size.

As shown in FIG. 4A, when the focus of the X-ray tube 102 is at FP1, the blade slot allows X-ray beams between lines L1 and L6 to pass through; when the focus of the X-ray tube is at FP2, the blade slot allows X-ray beams between lines L2 and L7 to pass through, and in the same manner, when the focus of the X-ray tube is at FP5, the blade slot allows X-ray beams between lines L5 and L10 to pass through.

The width of the blade slot and the positions of the inner and outer circular arcs thereof can be determined based on the requirement on the width of the X-ray detection area of the X-ray detector 112 during the CT scan, as well as the position and size of the various components of the CT system.

Figure 4B:
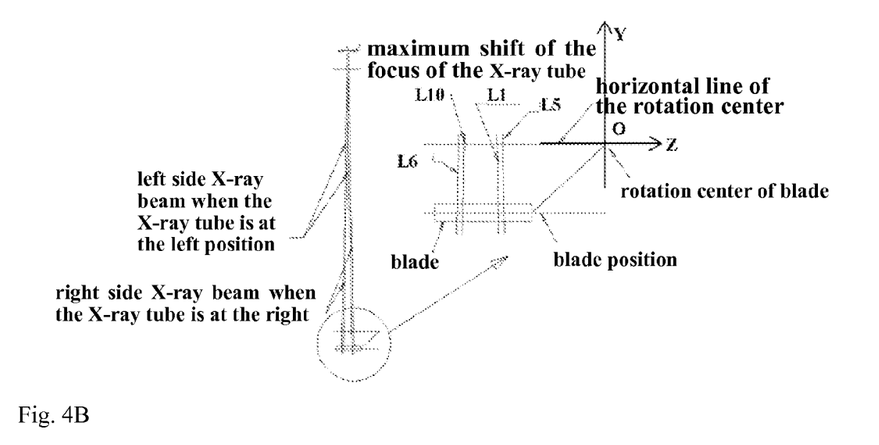
Figure 6A:
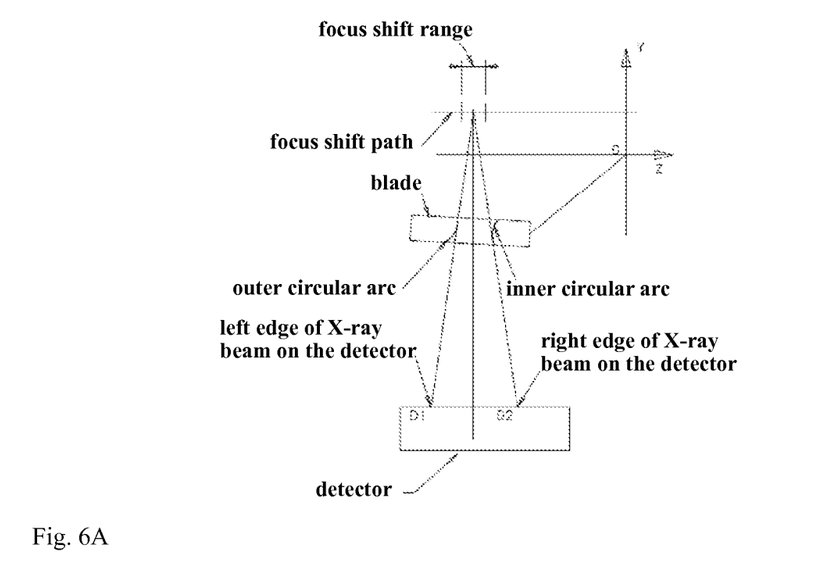
FIGS. 6A, 6B, 6C, and 6D show Z-beam tracking according to an exemplary embodiment of the present invention.

Specifically, as shown in FIG. 4B, a two-dimensional coordinate system YOZ is established using the rotation center O of the blade as the center of coordinate, wherein the horizontal line of the rotation center O is the OZ axis of the two-dimensional coordinate system. In the established two-dimensional coordinate system YOZ, the X-ray detection area of the X-ray detector 112 (namely, the edge points D1 and D2 of the X-ray detection area as shown in FIG. 6A), the position of the blade slot, the focus position of the X-ray tube 102 and the maximum shift position are known. Therefore, it is possible to determine, when the focus of the X-ray tube 102 is at the right maximum shift position FP5, the position of the X-ray line L10 that arrives at the left edge point D1 (see FIG. 6A) of the X-ray detection area of the X-ray detector 112 via the left edge point of the blade slot, and the position of the X-ray line L5 that arrives at the right edge point D2 (see FIG. 6A) of the X-ray detection area of the X-ray detector 112 via the right edge point of the blade slot in the two-dimensional coordinate system YOZ, and it is also possible to determine, when the focus of the X-ray tube 102 is at the left maximum shift position FP1, the position of the X-ray line L6 that arrives at the left edge point D1 of the X-ray detection area of the X-ray detector 112 via the left edge point of the blade slot, and the position of the X-ray line L1 that arrives at the right edge point D2 of the X-ray detection area of the X-ray detector 112 via the right edge point of the blade slot in the two-dimensional coordinate system YOZ.

Figure 4C:
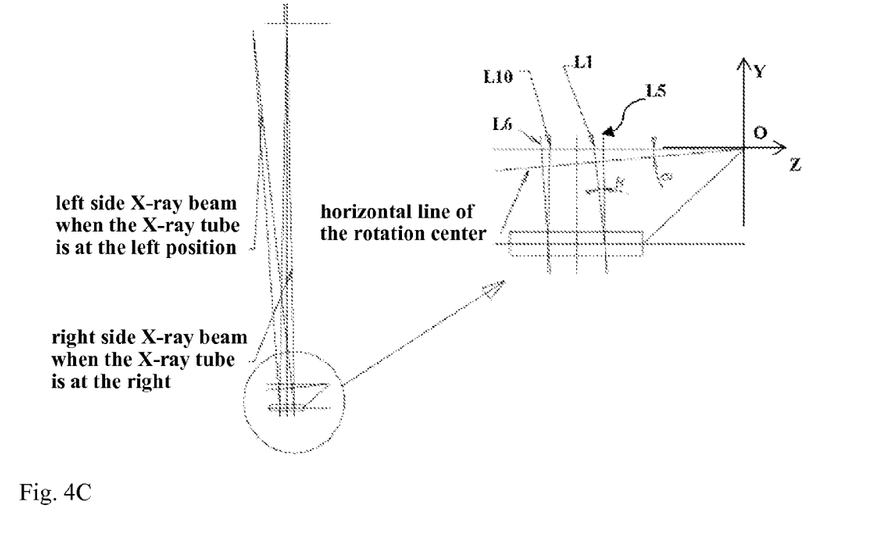

Still referring to FIG. 4B, maintain the positions of the X-ray lines L10 and L5 transmitted via the left and right edge points of the blade slot when the focus of the X-ray tube 102 is at the right maximum shift position FP5 unchanged and maintain the blade in a horizontal position, rotate the X-ray lines L6 and L1 transmitted via the left and right edge points of the blade slot when the focus of the X-ray tube 102 is at the left maximum shift position FP1 an angle of B around the blade rotation center O to enable lines L6 and L10 to have an intersection in the region along the thickness direction of the blade and to enable lines L1 and L5 to also have an intersection in the same region, as shown in FIG. 4C. If, during the rotation of the lines L6 and L1 around the blade rotation center O, the intersection of the lines L6 and L10 and the intersection of the lines L1 and L5 are not in the region along the thickness direction of the blade, then the thickness of the blade and the eccentricity between the blade slot and the rotation center O can be adjusted until the intersection of the lines L6 and L10 and the intersection of the lines L1 and L5 are in the region along the thickness direction of the blade, as the lines L6 and L1 rotate around the blade rotation center O.

Figure 4D:
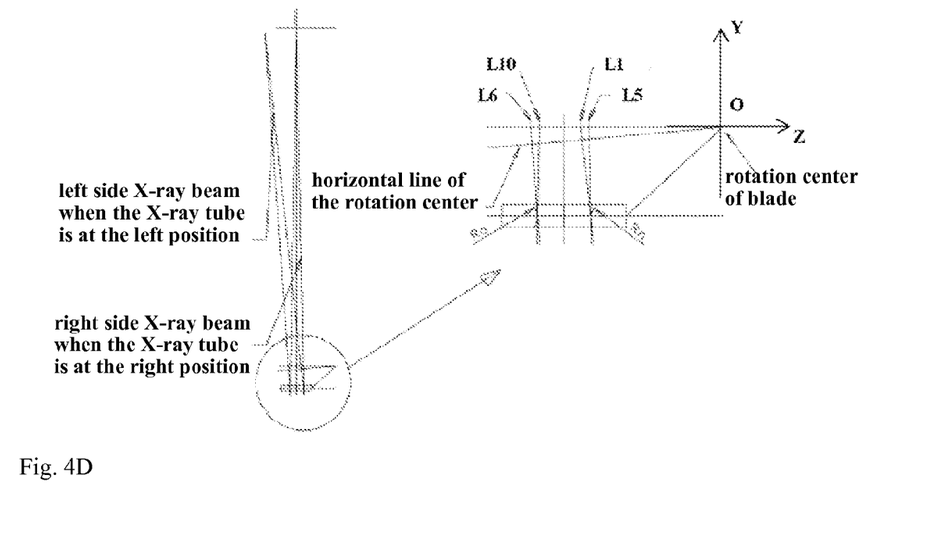

Thereafter, as shown in FIG. 4D, a predetermined radius Ro is used to set an outer circular arc near the intersection of lines L6 and L10 as described above, wherein the circle where the outer circular arc resides is tangent to the X-ray lines L6 and L10; similarly, a predetermined radius Rn is used to set an inner circular arc near the intersection of lines L1 and L5, wherein the circle where the inner circular arc resides is tangent to the X-ray lines L1 and L5, and wherein the width of the blade slot is determined by the inner and outer circular arcs as set above. The radii Ro and Rn of the outer and inner circular arcs may be set according to, for example, the requirement on the curvature of the outer and inner circular arcs. The radii Ro and Rn of the outer and inner circular arcs are appropriately selected so that the diameters of the circles where the outer and inner circular arcs reside are not less than the blade thickness. Besides, when relatively large values are selected for Ro and Rn, the outer and inner circular arcs should have an appropriate curvature so that the edges of the blade slot along the longitudinal direction have a convex curved surface structure.

In an embodiment, an equal angle tracking method similar to the above-described unequal angle tracking method or other similar methods may be used to determine the curved lines of the curved surface structure of each blade slot edge in a vertical plane along the longitudinal direction of the blade slot.

In an embodiment, after determining the shape of the curved surface structure of the edge of each blade slot edge in a vertical plane along the longitudinal direction of the blade slot, such as the inner and outer curved lines of the inner and outer circular arcs, the inner and outer curved lines are extended from the center position to the two ends of the slot in accordance with the shape of the slot edge, to enable the edges of the blade slot along the longitudinal direction to have convex curved surface structures, so that the X-rays projected on the X-ray detector 112 will have equal width in the Z direction. In an embodiment, the blade and the slot thereof may be divided into several slot segments, and the above-described unequal angle tracking method or equal angle tracking method is used to determine for each slot segment, the shape of the inner and outer curved lines (such as the inner and outer circular arcs) of the slot segment in the vertical plane along the longitudinal direction of the blade slot. Then the inner and outer curved lines are extended to said slot segment along the edge of the blade on which the slot segment is located, so as to form a convex curved surface structure on the blade slot edge of each slot segment, and finally form a convex curved surface structure for the edge of the entire blade slot along the longitudinal direction of the blade. In this way, the X-rays projected on the X-ray detector 112 will have equal width in the Z direction.

As described above, during operation of the X-ray tube 102, the focus thereof will shift as the temperature changes, thereby causing the X-ray detection area of the detector 112 to deviate from the initial X-ray detection area. Depending on the structure of the X-ray tube 102, the shift path of the focus of the X-ray tube can be a horizontal line, an oblique line, or other shapes. For simplicity, the following description is based on the example where the shift path of the focus of the X-ray tube is a horizontal line.

In the collimator 104 according to an embodiment of the present invention, when the focus of the X-ray tube 102 shifts, the collimator controller 120 can control the rotating slot part 2041 in the collimator 104 to rotate a certain angle to correct a route of the X-ray beam passing through the blade slot, so that the convex curved surface structure of the blade edge along the longitudinal direction of the blade can block some of the X-ray beams from the X-ray tube, thereby correcting the X-ray beams projected onto the X-ray detector 112, such that the X-ray detection area of the X-ray detector 112 remains unchanged when the focus of the X-ray tube 102 has changed. This tracking process is referred to as Z-beam tracking.

Next, reference will made to FIGS. 6A-6D to describe the Z-beam tracking process of an embodiment of the present invention in which the collimator 104 is controlled by the collimator controller 120 in a manner such that the X-ray detection area of the X-ray detector 112 remains unchanged when the focus the X-ray tube 102 shifts.

As shown in FIG. 6A, when the focus of the X-ray tube 102 is at the center of the focus shift range, the X-ray detection area of the X-rays projected to the X-ray detector 112 via the slot of the selected blade of the rotating slot part 2041 has a right edge point D2 and a left edge point D1, wherein focus shift range of the X-ray tube 102 depends on the structure of the X-ray tube 102. In an exemplary cross-sectional view of the center of the blade slot along the thickness direction perpendicular to the longitudinal direction of the blade, a two-dimensional coordinate system YOZ is established using the blade rotation center as the origin of coordinate. Based on the size, structure and the positional relationship of the various components of the CT system (including the X-ray tube 102, the collimator 104, the rotating slot part 2041 and blades of the collimator 104, and the X-ray detector 112), it is possible to determine the horizontal position of the selected blade of the plurality of blades of the rotating slot part 2041, the positions of the focus of the X-ray tube 102 and the X-ray detector 112, and the positions of the left and right edge points D1 and D2 in the X-ray detection region of the X-ray detector 112, in the established YOZ dimensional coordinate system.

Figure 6B:
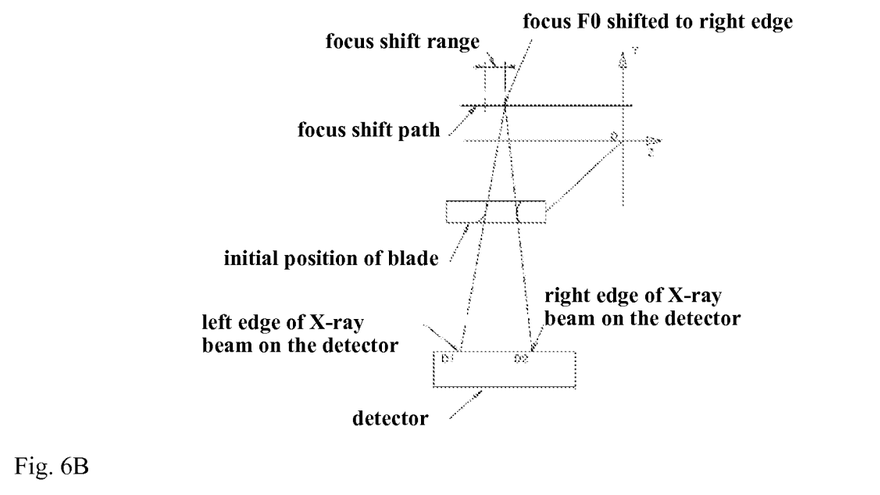

As shown in FIG. 6B, the right edge point F0 of the focus shift range of the X-ray tube 102 is selected as the initial reference position of the Z-beam tracking. As X-ray beams are projected to the X-ray detector 112 via the slot of the selected blade in the horizontal position, an X-ray detection area defined by the right edge point D2 and left edge point D1 is formed. It will be appreciated by persons skilled in the art that it is also possible to select one of other positions of the focus shift range as the initial reference position of the Z-beam tracking, as long as the X-ray detection area required for CT scan formed on the X-ray detector 112 by the X-ray beams passing through the slot of the selected blade are between the points D1 and D2.

Figure 6C:
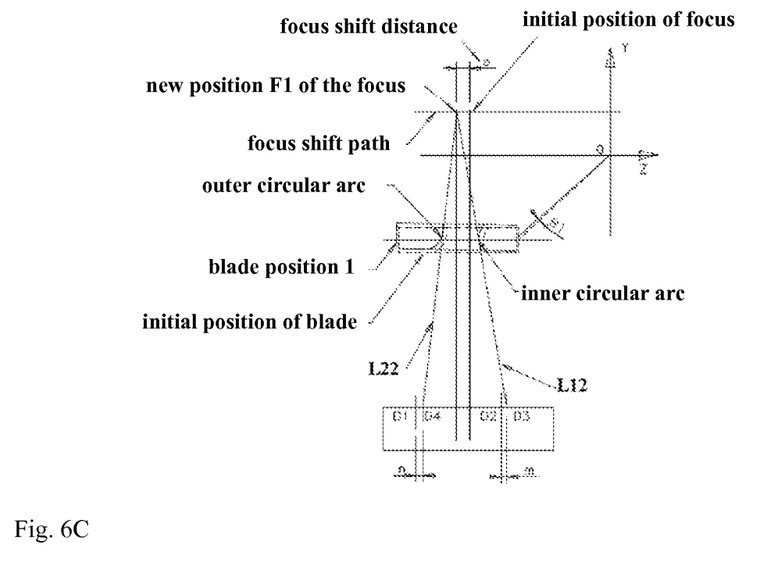

When the focus of the X-ray tube 102 shifts due to temperature change during a CT scan, for example, a left shift p along the focus shift path relative to the initial reference position of the focus as shown in FIG. 6C, a change will be caused to the X-ray detection area formed by projection of X-ray beams onto the X-ray detector 112 via the blade slot. The change of the X-ray detection area can be determined by an X-ray detection area offset monitoring unit provided on the X-ray detector 112.

In an embodiment, upon detection of a change of the X-ray detection area on the X-ray detector 112 by the X-ray detection area offset monitoring unit as compared with the X-ray detection area when the focus of the X-ray tube 102 is at the initial reference position, the blade may be in the horizontal position, which is compared to the position shown in FIG. 6B, the angle B1 of the blade is zero. The blade may also be in other locations, for example, in a position as shown in FIG. 6C, where the angle of the blade is B1 which may be determined by an encoder 2042 disposed in the collimator 104. As shown in FIG. 6C, the new X-ray detection area on the X-ray detector 112 has a right edge point D3 and a left edge point D4, which correspond to two X-rays L12 and L22, respectively. The two X-rays represent two edges of the X-ray beam allowed to pass through the slot between the inner circular arc and the outer circular arc of the selected blade. The X-ray detection area offset monitoring unit may send the determined offset of the X-ray detection area, namely, the distance m between point D3 and point D2 and/or the distance n between point D4 and point D1, to the collimator controller 120.

The encoder 2042 disposed in collimator 104 can measure an angle of rotation B1 of the selected blade around the rotation center O and send the measured angle B1 to the collimator controller 120. Based on the received angle B1 and the offset m and/or n of the X-ray detection area, as well as the positional relationships of the selected blade, the rotating slot part 2041, the X-ray tube 102, and the X-ray detector 112 in the two-dimensional coordinate system YOZ, the collimator controller 120 can determine the shift p of the focus of the X-ray tube 102 relative to the initial reference position.

Specifically, in an embodiment, the collimator controller 120 determines the position of the inner circular arc in the two-dimensional coordinate system YOZ based on the angle B1 measured by the encoder 2042 and the radius of rotation of the selected blade around the rotation center O. Then, based on the offset m of the X-ray detection area determined by the X-ray detection area offset monitoring unit, as well as the positional relationships of the selected blade, the rotating slot part 2041, the X-ray tube 102, and the X-ray detector 112 in the two-dimensional coordinate system YOZ, the collimator controller 120 determines a straight line L12 passing point D3 and tangent to the inner circular arc in the two-dimensional coordinate system YOZ, wherein the straight line L12 represents the rightmost X ray of the X-ray beam when the focus of the X-ray tube 102 shifts from the right edge point F0 to the new position F1, and the selected blade is at the rotation angle B1. The intersection point of the determined line L12 and the focus shift path of the X-ray tube 102 is the new position F1 of the shifted focus of the X-ray tube 102.

In an embodiment, the collimator controller 120 determines the position of the outer circular arc in the two-dimensional coordinate system YOZ based on the rotation angle B1 of the selected blade, the radius of rotation of the selected blade around the rotation center O, the position of the inner circular arc and the positional relationship of the inner and outer circular arcs. Then, based on the offset n determined by the X-ray detection area offset monitoring unit, as well as the positional relationships of the selected blade, the rotating slot part 2041, the X-ray tube 102, and the X-ray detector 112 in the two-dimensional coordinate system YOZ, the collimator controller 120 determines a straight line L22 passing point D4 and tangent to the outer circular arc in the two-dimensional coordinate system YOZ, wherein the straight line L22 represents the leftmost X ray of the X-ray beam when the focus of the X-ray tube 102 shifts from the right edge point F0 to the new position F1, and the selected blade is at the rotation angle B1. The intersection point of the determined line L22 and the focus shift path of the X-ray tube 102 is the new position F1 of the shifted focus of the X-ray tube 102.

In an embodiment, after the collimator controller 120 determines two focus shift new positions F1 based on the straight lines L12 and L22 in the two-dimensional coordinate system YOZ respectively, an average of the two new positions is used as the final focus shift new position F1.

The collimator controller 120 may, after determining the focus shift p of the X-ray tube 102 along the focus shift path and the rotation angle B1 of the selected blade, determine a rotation correction angle of the blade needed for eliminating of the offsets m and n of the X-ray detector region on the X-ray detector 112, and then cause the rotating slot part 2041, driven by the motor drive system 2043, to rotate said correction angle about the center of the rotation shaft 2042, so that the X-ray detection area formed by projection of X rays to the X-ray detector 112 via the slot of the selected blade remains unchanged as the focus of the X-ray tube 102 shifts to a new location F1 along the focus shift path relative to the initial reference position F0, thereby completing Z-beam tracking for focus shift of the X-ray tube 102.

Figure 6D:
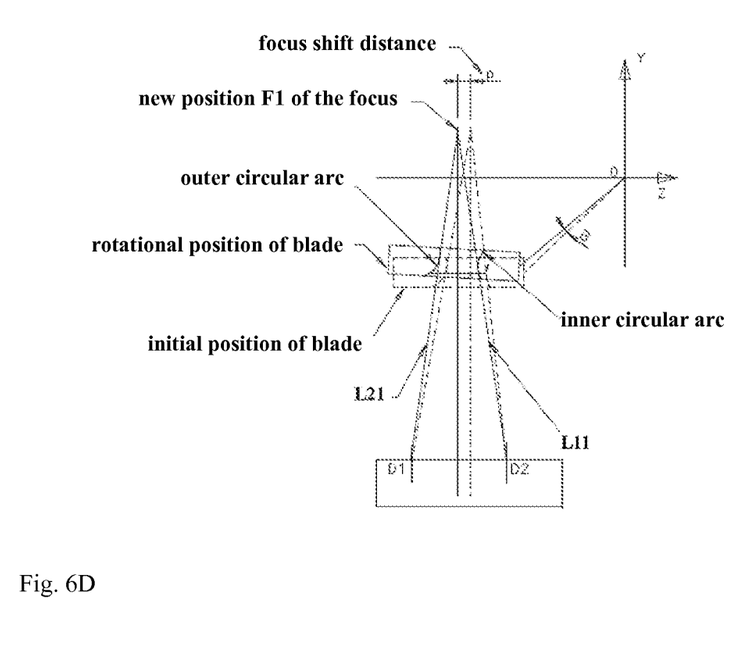

Specifically, as shown in FIG. 6D, in an embodiment, after determining the focus shift p of the X-ray tube 102, the collimator controller 120 can determine the position of the new position F1 of the focus in the two-dimensional coordinate system YOZ, and then determine a straight line L11 passing point F1 and point D2 in the two-dimensional coordinate system YOZ based on the determined new position F1 of the focus and the right edge point D2 of the initial X-ray detection area on the X-ray detector 112. When the X-ray detection area obtained on the X-ray detector 112 via the blade slot is remained unchanged as a result of the blade rotating a correction angle about the rotation center O after the focus of the X-ray tube 102 has shifted a distance of p along the focus shift path, the inner circular arc of the slot of the selected blade is tangent to the X-ray at line L11 in the two-dimensional coordinate system YOZ. Therefore, in the case that the line L11 is known, the correction angle B that the blade rotates around the rotation center O can be determined based on the positional relationship that the inner circular arc is tangent to line L11 and such known parameters as the radius of rotation of the blades.

In an embodiment, after determining the position of the new position F1 of the focus in the two-dimensional coordinate system YOZ, the collimator controller 120 then determines a straight line L21 passing point F1 and point D1 in the two-dimensional coordinate system YOZ based on the determined new position F1 of the focus and the left edge point D1 of the initial X-ray detection area on the X-ray detector 112. When the X-ray detection area obtained on the X-ray detector 112 via the blade slot is remained unchanged as a result of the blade rotating a correction angle about the rotation center O after the focus of the X-ray tube 102 has shifted a distance of p along the focus shift path, the outer circular arc of the slot of the selected blade is tangent to the X-ray at line L21 in the two-dimensional coordinate system YOZ. Therefore, in the case that the line L21 is known, the correction angle B that the blade rotates around the rotation center O can be determined based on the positional relationship that the outer circular arc is tangent to line L21, the positional relationship of the inner and outer circular arcs of the blade slot, and such known parameters as the radius of rotation of the blade.

In an embodiment, the collimator controller 120 may, after determining two correction angles B that the blade rotates around the rotation center O based on the straight lines L11 and L21 respectively, use an average of the two values as the final correction angle B for performing the Z-beam tracking.

Alternatively, the collimator controller 120 is further configured to, after completing a first Z-beam tracking for the focus shift of the X-ray tube 102, compare the offset m and/or n of the X-ray detection area determined in real time by the X-ray detection area monitoring unit with a predetermined threshold. If the offset m and/or n determined in real time do not exceed their respective thresholds, the Z-beam tracking is completed. If the offset m and/or n determined in real time exceed their respective thresholds, then the above procedure of Z-beam tracking may be repeated until the latest offset m and/or n of the X-ray detection area do not exceed their respective thresholds.

In an embodiment, a plurality of focus shifts p of the X-ray tube 102 along the focus shift path during a CT scan and a plurality of corresponding correction angles B (including the rotation direction) that the selected blade is required to rotate for achieving Z-beam tracking may be predetermined for each blade in the rotating slot part 2041 based on simulation or actual measurements. The plurality of shifts p and the corresponding correction angles B are stored in the form of a table in a memory within the collimator controller 120 or in an external memory coupled to the collimator controller 120 (not shown). When the focus of the X-ray tube 102 shifts along the focus shift path due to temperature change during a CT scan of the subject 114, the collimator controller 120 can determine the focus shift p of the X-ray tube based on the offset m and/or n of the X-ray detection area determined by the X-ray detection area monitoring unit arranged on the X-ray detector 112, search in the memory for a blade rotation correction angle B corresponding to the focus shift p of the X-ray tube, and then cause the blade to rotate said correction angle around the rotation center under the action of the motor drive system 2043, based on the blade rotation correction angle B found and the current angle B1 of the blade determined by the encoder 2042, thereby eliminating the offset m and/or n of the X-ray detection area on the X-ray detector 112 and achieving Z-beam tracking.

If the collimator controller 120 fails to find a focus shift p of the X-ray tube in the memory, then it can search for two correction angles B corresponding to two focus shifts close to the focus shift p of the X-ray tube; based on the relationship between the focus shift p of the X-ray tube and the two adjacent focus shifts thereof, a final correction angle B can be determined by performing an interpolation between the two correction angles B found. In an embodiment, if the collimator controller 120 fails to find a focus shift p of the X-ray tube in the memory, a correction angle B corresponding to the focus shift closest to the focus shift p of the X-ray tube can be searched for and used as the final correction angle B. In an embodiment, if the collimator controller 120 fails to find a focus shift p of the X-ray tube in the memory, it can search for two correction angles B corresponding to two focus shifts close to the focus shift p of the X-ray tube, and then use an average of the two correction angles B as the final correction angle B.

In an embodiment, a plurality of offsets m and/or n of the X-ray detection area on the X-ray detector 112 and a plurality of corresponding correction angles B (including the rotation direction) that the blade is required to rotate for achieving Z-beam tracking may be predetermined based on simulation or actual measurements. The plurality of offsets m and/or n of the X-ray detection area and the corresponding correction angles B are stored in the form of a table in a memory within the collimator controller 120 or in an external memory coupled to the collimator controller 120 (not shown). When the focus of the X-ray tube 102 shifts along the focus shift path due to temperature change during a CT scan of the subject 114, the collimator controller 120 can search for a corresponding blade rotation correction angle B in the memory based on the offset m and/or n of the X-ray detection area determined by the X-ray detection area monitoring unit arranged on the X-ray detector 112, and then cause the blade to rotate said correction angle around the rotation center under the action of the motor drive system 2043, based on the blade rotation correction angle B found and the current angle B1 of the blade determined by the encoder 2042, thereby eliminating the offset m and/or n of the X-ray detection area on the X-ray detector 112 and achieving Z-beam tracking.

If the collimator controller 120 fails to find an offset m and/or n of the X-ray detection area determined by the X-ray detection area monitoring unit in the memory, then it can search for two correction angles B corresponding to two offsets close to the offset m and/or n of the X-ray detection area; based on the relationship between the offset m and/or n of the X-ray detection area and the two close offsets thereof, a final correction angle B can be determined by performing an interpolation between the two correction angles B found. In an embodiment, if the collimator controller 120 fails to find an offset m and/or n of the X-ray detection area determined by the X-ray detection area monitoring unit in the memory, a correction angle B corresponding to the offset closest to the offset m and/or n of the X-ray detection area can be searched for and used as the final correction angle B. In an embodiment, if the collimator controller 120 fails to find an offset m and/or n of the X-ray detection area determined by the X-ray detection area monitoring unit in the memory, it can search for two correction angles B corresponding to two offsets close to the offset m and/or n of the X-ray detection area, and then use an average of the two correction angles B as the final correction angle B.

Returning to FIG. 5, when the focus of the X-ray tube 102 shifts along the focus shift path due to temperature change, the collimator controller 120 controls the selected blade in the collimator 104 to rotate a correction angle about the rotation center to eliminate an offset of the X-ray detection area formed by projection of X-rays to the X-ray detector 112 via the slot of the selected blade, so that the X-ray detection area is substantially restored to the initial position when no focus shift takes place. As shown, after performing Z-beam tracking, the X-ray detection area A2 obtained on the X-ray detector 112 is substantially consistent with the X-ray detection area A1 before focus shift. Simulation and actual measurements also show that after Z-beam tracking the X-ray detection area A2 obtained on the X-ray detector 112 has extremely little difference as compared with the X-ray detection area A1 before focus shift. Accurate tracking is achieved at the D2 side of the X-ray detection area on the X-ray detector 112, slight difference is observed in the D1 side, and accurate tracking is achieved at leftmost and rightmost positions with respect to the angle shift of the X-ray tube.

The CT collimator according to an embodiment of the present invention uses a single motor drive system to perform slot width selection and Z-beam tracking during a CT scan. As compared with conventional CT collimators using at least two or more motor drive systems, the CT collimator according to an embodiment of the present invention achieves a lower manufacturing cost. By using a single motor drive system to directly drive the rotating slot part of the collimator, the present collimator requires no rails, ball screw or lead screw, and thus has a simpler structure than a conventional collimator, and hence higher reliability and better maintainability. In the CT collimator according to an embodiment of the present invention, according to needs of CT scans, the rotating slot part can be provided with a plurality of blades having different slot widths. The edges of each blade slot along the longitudinal direction of the blade have convex curved surface structures, so that when a focus shift of the radiation source along a focus shift path occurs as a result of temperature change, by rotating the selected blade about a rotation center eccentric to the blade a correction angle corresponding to the focus shift, the radiation beam reaching the radiation detector via the blade slot is maintained at the same region and same width as the circumstance when no focus shift takes place. Therefore, the CT collimator and CT system according to an embodiment of the present invention eliminate the need of extra adjustment of the components such as the radiation detector when a focus shift of the radiation source occurs.

Although the present invention has been described with reference to specific embodiments, it shall be understood that the present invention is not limited to these specific embodiments. Skilled in the art will appreciate that various modifications, substitutions, changes and so on may be made to the present invention. For example, in the above embodiments one step or component may be divided into multiple steps or components; or, on the contrary, a plurality of steps or components in the above embodiments may be realized in one step or one component. All such variations should be within the scope of protection as long as they do not depart from the spirit of the present invention. In addition, the terms as used in the present specification and claims are not limitative, but descriptive. Moreover, according to actual needs, the entire or part of the features described in one specific embodiment can be incorporated into another embodiment.

What is claimed is:

1. A CT collimator, comprising:
   a rotating slot part disposed on a rotation shaft and comprising a plurality of blades,
   wherein each blade comprises a slot of a different width and a radiation beam entering the collimator can only pass via a slot in one of the plurality of blades,
   wherein each edge of each slot along a longitudinal direction of the corresponding blade comprises a convex curved surface structure, and in a vertical plane along a longitudinal direction of the slot, two side edges of the slot are curved, and
   wherein each blade is arranged to be eccentric to a center of the rotation shaft.

2. The CT collimator as claimed in claim 1, further comprising:
   a single motor configured to drive the rotating slot part to rotate around the rotation shaft; and
   an encoder configured to monitor an angle of rotation of the rotating slot part around the center of the rotation shaft.

3. The CT collimator as claimed in claim 1, further comprising:
   a single motor configured to drive the rotating slot part to rotate around the rotation shaft,
   wherein the single motor comprises an encoder configured to monitor an angle of rotation of the rotating slot part around the center of the rotation shaft.

4. The CT collimator as claimed in claim 1, wherein the convex curved surface structure of each edge comprises two curved lines in a vertical plane along the longitudinal direction of the corresponding blade, and the slot of the corresponding blade allows radiation beams between radiation lines tangent to the two curved lines to pass through.

5. The CT collimator as claimed in claim 1, wherein the convex curved surface structure of each edge comprises two circular arcs in a vertical plane along the longitudinal direction of the corresponding blade, and the slot of the corresponding blade allows radiation beams between radiation lines tangent to the two circular arcs to pass through.

6. The CT collimator as claimed in claim 5, wherein the two circles for the two circular arcs are respectively: when, in the vertical plane, the rotation of a first connecting line and a second connecting line between a maximum shift position to the left of a radiation source and left and right edge points of a radiation detection area of a radiation detector about the center of the rotation shaft relative to a third connecting line and a fourth connecting line between a maximum shift position to the right of the radiation source and the left and right edge points of the radiation detection area reaches a position where there are respective intersections in a blade thickness region between the first connecting line and the third connecting line and between the second connecting line and the fourth connecting line, a first circle that is tangent to the first connecting line and the third connecting line at the position, and a second circle that is tangent to the second connecting line and the fourth connecting line at the position.

7. The CT collimator as claimed in claim 1, wherein each blade comprises a planar structure, and a width of a slot of each blade gradually increases from a center of the slot to two ends thereof along the longitudinal direction of the blade.

8. The CT collimator as claimed in claim 1, wherein when each blade comprises an arc structure whose center of circle is on a focal point of a radiation source outside the collimator when the blade is located in a horizontal position.

9. The CT collimator as claimed in claim 1, wherein when the center of the rotation shaft is not located in an extended region of each slot along a thickness direction of the corresponding blade, the corresponding blade is eccentric to the center of the rotation shaft.

10. A CT system comprising:
    a CT collimator comprising:
       a rotating slot part disposed on a rotation shaft and comprising a plurality of blades,
       wherein each blade comprises a slot of a different width and a radiation beam entering the collimator can only pass via a slot in one of the plurality of blades, wherein each edge of each slot along a longitudinal direction of the corresponding blade comprises a convex curved surface structure, and in a vertical plane along a longitudinal direction of the slot, two side edges of the slot are curved, and wherein each blade is arranged to be eccentric to a center of the rotation shaft;

a radiation detection area monitoring unit disposed on a radiation detector; and a collimator controller configured to select one of the plurality of blades of the rotating slot part according to a region of interest of a subject to allow a desired radiation beam to be projected to the region of interest of the subject, wherein the radiation detection area monitoring unit monitors, during a CT scan, an offset of a radiation detection area on the radiation detector caused by focus shift of a radiation source as a radiation beam is projected to the radiation detector via the selected blade of the CT collimator, and wherein the collimator controller is configured to correct an angle of rotation of the rotating slot part of the CT collimator according to the monitored offset received from the radiation detection area monitoring unit to eliminate the offset of the radiation detection area caused by the focus shift of the radiation source to perform Z-beam tracking.

11. The CT system as claimed in claim 10, wherein the CT system is an X-ray CT system.

12. The CT system as claimed in claim 10, wherein the collimator controller comprises a memory or is coupled to a memory.

13. The CT system as claimed in claim 12, wherein a plurality of offsets of the radiation detection area predetermined for each blade in the rotating slot part and a plurality of corresponding correction angles that the rotating slot part is required to rotate to perform Z-beam tracking are stored in the form of a table in the memory.

14. The CT system as claimed in claim 13, wherein the collimator controller is further configured to:
 determine a rotation correction angle of the rotating slot part for the selected blade through a search in the table in the memory according to the monitored offset of the radiation detection area, and
 perform Z-beam tracking according to the determined rotation correction angle of the rotating slot part and a current angle of the selected blade.

15. The CT system as claimed in claim 14, wherein the collimator controller is further configured to:
 in case of failure to find a corresponding rotation correction angle of the rotating slot part in the table according to the monitored offset of the radiation detection area, search for two rotation correction angles corresponding to two offsets close to the monitored offset of the radiation detection area, and use an average of the two rotation correction angles or an interpolation therebetween as the determined rotation correction angle of the rotating slot part, or
 in case of failure to find a corresponding rotation correction angle of the rotating slot part in the table according to the monitored offset of the radiation detection area, search for a rotation correction angle corresponding to a shift closest to the monitored offset of the radiation detection area and use it as the determined rotation correction angle of the rotating slot part.

16. The CT system as claimed in claim 12, wherein a plurality of focus shifts of the radiation source predetermined for each blade in the rotating slot part and a plurality of correction angles that the rotating slot part is required to rotate to perform Z-beam tracking are stored in the form of a table in the memory.

17. The CT system as claimed in claim 16, wherein the collimator controller is configured to:
 determine a focus shift of the radiation source according to the monitored offset of the radiation detection area,
 determine a rotation correction angle of the rotating slot part for the selected blade through a search in the table in the memory according to the determined focus shift, and
 perform Z-beam tracking according to the determined rotation correction angle of the rotating slot part and the current angle of the selected blade.

18. The CT system as claimed in claim 17, wherein the collimator controller is further configured to:
 in case of failure to find a corresponding rotation correction angle of the rotating slot part in the table according to the determined focus shift, search for two rotation correction angles corresponding to two focus shifts close to the determined focus shift, and use an average of the two rotation correction angles or an interpolation therebetween as the determined rotation correction angle of the rotating slot part; or
 in case of failure to find a corresponding rotation correction angle of the rotating slot part in the table according to the determined focus shift, search for a rotation correction angle corresponding to the focus shift closest to the determined focus shift and use it as the determined rotation correction angle of the rotating slot part.

19. The CT system as claimed in claim 10, wherein the collimator controller is further configured to, after correction of a rotation angle of the rotating slot part of the CT collimator, compare a latest monitored offset of the radiation detection area received from the radiation detection area monitoring unit with a predetermined threshold, and if the latest monitored offset of the radiation detection area does not exceed the predetermined threshold, then stop a Z-beam tracking; or, if the latest monitored offset of the radiation detection area exceeds the predetermined threshold, then perform a new Z-beam tracking until the latest monitored offset of the radiation detection area does not exceed the predetermined threshold.

* * * * *

UNITED STATES PATENT AND TRADEMARK OFFICE
CERTIFICATE OF CORRECTION

PATENT NO. : 9,014,341 B2
APPLICATION NO. : 14/071178
DATED : April 21, 2015
INVENTOR(S) : Zhang et al.

Page 1 of 1

It is certified that error appears in the above-identified patent and that said Letters Patent is hereby corrected as shown below:

In the Specification

In Column 5, Line 32, delete "X-ray detector 124" and insert -- X-ray detector 112 --, therefor.

In Column 6, Line 37, delete "X-ray tube 104" and insert -- X-ray tube 102 --, therefor.

In Column 12, Line 42, delete "rotation shaft 2042," and insert -- rotation shaft 2044, --, therefor.

Signed and Sealed this
Twenty-second Day of September, 2015

Michelle K. Lee
*Director of the United States Patent and Trademark Office*